US009913665B2

(12) United States Patent
Biedermann et al.

(10) Patent No.: US 9,913,665 B2
(45) Date of Patent: Mar. 13, 2018

(54) RECEIVING PART OF A BONE ANCHORING DEVICE AND BONE ANCHORING DEVICE WITH SUCH A RECEIVING PART

(71) Applicant: BIEDERMANN TECHNOLOGIES GMBH & CO. KG, Donaueschingen (DE)

(72) Inventors: Lutz Biedermann, VS-Villingen (DE); Timo Biedermann, Trossingen (DE); Wilfried Matthis, Weisweil (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 0 days.

(21) Appl. No.: 15/177,665

(22) Filed: Jun. 9, 2016

(65) Prior Publication Data

US 2016/0361093 A1 Dec. 15, 2016

Related U.S. Application Data

(60) Provisional application No. 62/173,870, filed on Jun. 10, 2015.

(30) Foreign Application Priority Data

Jun. 10, 2015 (EP) .................................... 15171533

(51) Int. Cl.
    *A61B 17/70* (2006.01)
(52) U.S. Cl.
    CPC ...... *A61B 17/7032* (2013.01); *A61B 17/7037* (2013.01)
(58) Field of Classification Search
    CPC .............. A61B 17/708; A61B 17/7083; A61B 17/7085; A61B 17/7086; A61B 17/7088
    See application file for complete search history.

(56) References Cited

U.S. PATENT DOCUMENTS

8,518,082 B2   8/2013  Sicvol et al.
8,617,210 B2*  12/2013 Sicvol ................ A61B 17/7032
                                                      606/246

(Continued)

FOREIGN PATENT DOCUMENTS

DE   199 51 145 A1   5/2001
EP   2 826 429 A1    1/2015

OTHER PUBLICATIONS

European Search Report dated Dec. 8, 2015 for Application No. 15171533.1; (8 Pages).

*Primary Examiner* — Jan Christopher Merene
*Assistant Examiner* — Atiya Mahmud
(74) *Attorney, Agent, or Firm* — Lewis Roca Rothgerber Christie LLP (57) ABSTRACT

A receiving part of a bone anchoring device is provided, where the receiving part includes a first end, a second end opposite to the first end, a central axis extending through the first end and the second end, and a substantially U-shaped-recess adjacent to the first end for receiving a spinal fixation element. The substantially U-shaped recess forms two free legs. The receiving part also includes a bore extending from the first end towards the second end and in communication with the substantially U-shaped recess. A groove is provided in an outer surface of each of the legs, where the groove has a first end and a second end and extends in a circumferential direction in an arcuate shape between the first end of the groove and the second end of the groove. In a plane that includes the central axis and that extends through a center of each leg, a contour of a surface of the groove has at least a first arcuate portion and a second arcuate portion opposing the first arcuate portion, where the contour is substantially free from straight portions.

21 Claims, 9 Drawing Sheets

(56) References Cited

U.S. PATENT DOCUMENTS

| | | | |
|---|---|---|---|
| 8,795,283 B2* | 8/2014 | Petit | A61B 17/708 606/86 A |
| 2002/0120272 A1* | 8/2002 | Yuan | A61B 17/7032 606/276 |
| 2005/0131408 A1 | 6/2005 | Sicvol et al. | |
| 2006/0173456 A1* | 8/2006 | Hawkes | A61B 17/7037 606/278 |
| 2008/0147129 A1* | 6/2008 | Biedermann | A61B 17/7032 606/308 |
| 2009/0222045 A1* | 9/2009 | Gorek | A61B 17/0206 606/279 |
| 2012/0095516 A1* | 4/2012 | Dikeman | A61B 17/7032 606/305 |
| 2012/0253408 A1* | 10/2012 | Timm | A61B 17/7037 606/305 |
| 2013/0103094 A1* | 4/2013 | Beale | A61B 17/7076 606/279 |
| 2014/0094849 A1 | 4/2014 | Spratt et al. | |
| 2015/0039035 A1* | 2/2015 | Kruger | A61B 17/7037 606/264 |
| 2016/0113682 A1* | 4/2016 | Altarac | A61B 17/7085 606/265 |

* cited by examiner

RECEIVING PART OF A BONE ANCHORING DEVICE AND BONE ANCHORING DEVICE WITH SUCH A RECEIVING PART

CROSS-REFERENCE TO RELATED APPLICATIONS

The present application claims the benefit of U.S. Provisional Application Ser. No. 62/173,870, filed Jun. 10, 2015, the contents of which are hereby incorporated by reference in their entirety, and claims priority to European Patent Application EP 15 171 533.1, filed Jun. 10, 2015, the contents of which are hereby incorporated by reference in their entirety.

BACKGROUND

Field

The present disclosure relates to a receiving part of a bone anchoring device, where the receiving part includes a substantially U-shaped recess for receiving a spinal fixation element, the substantially U-shaped recess forming two free legs, and where each leg has a groove in an outer surface thereof for engaging an instrument. In particular, the receiving part is configured for use with an instrument suitable for MIS (minimally invasive surgery). The present disclosure further relates to a bone anchoring device having such a receiving part and a system of a bone anchoring device and an instrument, in particular for minimally invasive surgery.

Description of the Related Art

U.S. Pat. No. 8,518,082 B2 describes a percutaneous access device which includes an inner tube and an outer tube. A bone anchor assembly is described including a bone anchor having a distal bone engaging portion and a receiving member having a recess for receiving a spinal fixation element. The proximal end of the receiving member may have an arcuate groove formed on an exterior surface thereof to facilitate connection of an instrument to the receiving member. The arcuate groove has a proximal surface and a distal surface opposite the proximal surface. The proximal surface and the distal surface are each angled distally towards an exterior surface of legs of the receiving part and each are oriented at an angle greater than 0° relative to an orthogonal line that is oriented perpendicular to a longitudinal axis of the receiving member. In another embodiment, the proximal surface is oriented at an angle between approximately 5° and 30° relative to an orthogonal line that is oriented perpendicular to the longitudinal axis of the receiving member.

SUMMARY

Embodiments of the invention provide an improved receiving part for a bone anchoring device, and a bone anchoring device with such a receiving part that facilitates and/or supports engagement of the receiving part with an instrument, in particular with a MIS instrument, and that has a simple design. Furthermore, a system of such a receiving part and an instrument is provided.

A groove is provided in an exterior surface of the receiving part and is defined by a single curved surface that may have a plurality of portions with different curvatures and that is substantially free from flat surface portions. Substantially free from flat surface portions means that there are no flat surface portions between arcuate portions. The curved surface of the groove facilitates engagement of the receiving part with an instrument, such as by hooking-in of the instrument, in particular, the groove facilitates sliding of an engagement portion of the instrument into the groove. This is particularly suitable for using the bone anchoring device in a MIS procedure with MIS instruments, such as head extension devices.

The receiving part can be manufactured in an easy and cost-efficient manner.

Moreover, with the curved surface of the groove, notching effects during engagement with the instrument are reduced. Hence, the receiving part is more robust as compared to other receiving parts that have angled surface portions for engagement with an instrument. Furthermore, it is not necessary to specifically adapt an instrument to the particular shape of the groove of the receiving part.

The receiving part can be combined with existing instruments. This increases the variety of applications of the receiving part.

A bone anchoring device including such a receiving part may be realized in any form, such as a top or a bottom loading polyaxial bone anchoring device, a bone anchoring device with a receiving part using an inner compression member or an outer ring for locking an angular position of the anchoring element, or as a monoaxial bone anchoring device.

BRIEF DESCRIPTION OF THE DRAWINGS

Further features and advantages of the invention will become apparent from the description of embodiments by means of the accompanying drawings. In the drawings:

FIG. 4b shows an enlarged cross-sectional view of a detail of FIG. 4a;

FIG. 5 shows a side view of the bone anchoring device of FIGS. 1 to 4b with a portion of an instrument attached thereto;

FIG. 6a shows a cross-sectional view of the bone anchoring device of FIGS. 1 to 5 with a portion of the instrument of FIG. 5;

FIG. 6b shows an enlarged cross-sectional view of a detail of FIG. 6a;

FIG. 9a shows a cross-sectional view of the bone anchoring device of FIGS. 7 and 8, where the cross-section is taken in a plane including a central axis of the receiving part and extending through centers of the legs of the receiving part;

FIG. 9b shows an enlarged cross-sectional view of a detail of FIG. 9a;

FIG. 12a shows a cross-sectional view of the bone anchoring device of FIGS. 10 and 11, where the cross-section is taken in a plane including a central axis of the receiving part and extending through centers of the legs of the receiving part;

FIG. 12b shows an enlarged cross-sectional view of a detail of FIG. 12a;

FIG. 14b shows an enlarged cross-sectional view of a detail of FIG. 14a;

FIG. 16b shows an enlarged cross-sectional view of a detail in FIG. 16a.

DETAILED DESCRIPTION

As shown in FIGS. 1 to 4b, a bone anchoring device according to a first embodiment includes an anchoring element 1 with shank 2 having a bone thread in at least a portion thereof and a spherical segment-shaped head 3. The shank 2 may be cannulated. An engagement portion 4 may be provided at a free end surface of the head 3. The anchoring element 1 is pivotably coupled to a receiving part 5. A pressure element 6 is configured to exert pressure onto the head 3 to lock an angular position of the bone anchoring element 1 relative to the receiving part 5. The receiving part 5 serves for coupling the bone anchoring element 1 to a spinal fixation element, such as a spinal rod (not shown) that can be inserted into the receiving part 5 and fixed by a locking element (not shown), such as a set screw.

The receiving part 5 may be formed as a substantially cylindrical part with a first end or top end 5a, an opposite second end or bottom end 5b, a central axis C that may be an axis of symmetry, a coaxial bore 51 extending from the first end 5a to a distance from the second end 5b, a seat 52 for the head 3 of the bone anchoring element 1, and a lower opening 53 at the bottom end 5b. The seat 52 may have a spherical shape adapted to a shape of the head 3, but may also have any other shape that is suitable for allowing a pivoting motion of the head 3 in the seat 52, such as a conically narrowing shape. Adjacent to the first end 5a, an advancement structure 54, such as an internal thread, may be provided for allowing the locking element to be advanced into the bore 51.

A substantially U-shaped recess 55 extends from the first end 5a towards the second end 5b. The recess 55 serves for receiving the longitudinal spinal fixation element (not shown) therein, such as a rod. The recess 55 forms two free legs 56a, 56b. In an outer surface of each of the legs 56a, 56b, circumferentially extending grooves 57a, 57b are formed for engagement with an instrument that holds the receiving part 5 during a surgical procedure. The grooves 57a, 57b are located at a distance from the first end 5a in the axial direction of the receiving part 5.

Figure 1:
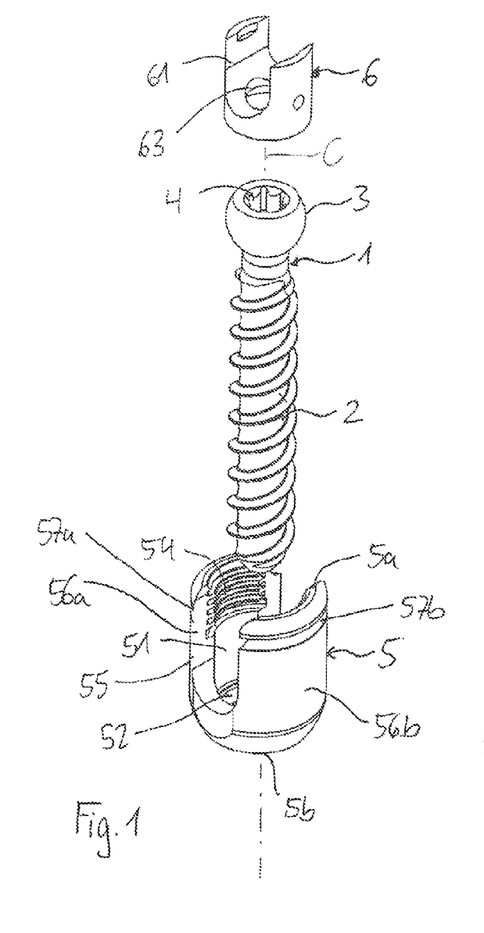
FIG. 1 shows an exploded perspective view of a bone anchoring device with a receiving part according to a first embodiment.
Figure 2:
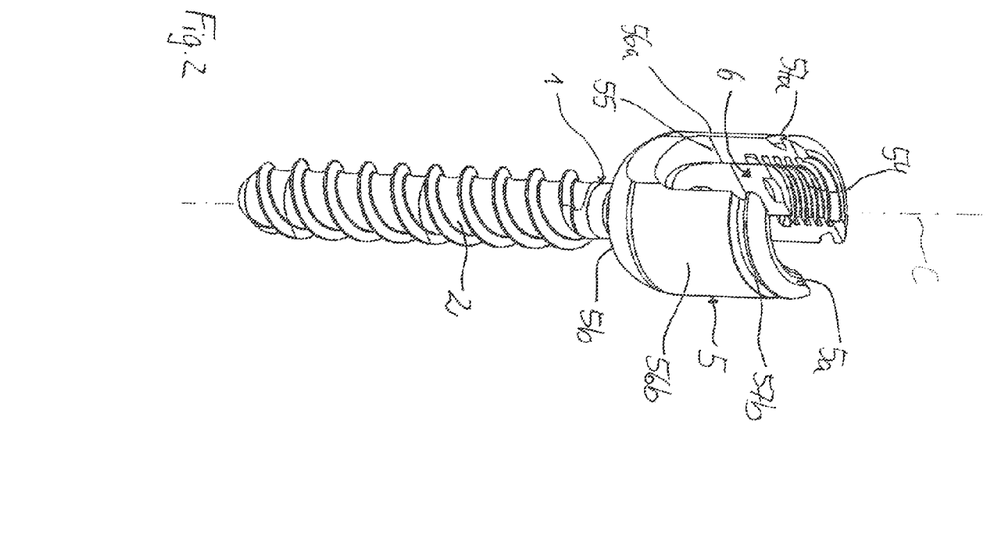
FIG. 2 shows a perspective view of the bone anchoring device of FIG. 1 in an assembled state.
Figure 3:
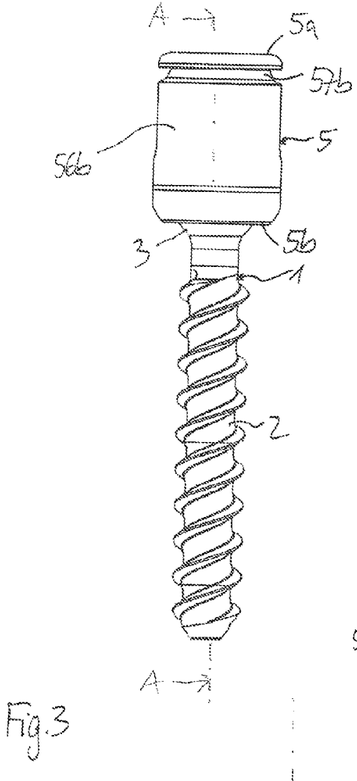
FIG. 3 shows a side view of the bone anchoring device of FIGS. 1 and 2.

In the circumferential direction, the grooves 57a, 57b respectively extend along an entire width of each leg 56a, 56b from one end of a channel formed by the U-shaped recess 55 to a second end of the channel and have ends that are open towards the U-shaped recess 55. Because of the substantially cylindrical shape of the receiving part 5, the grooves 57a, 57b have an arcuate shape in the circumferential direction with a center of curvature lying on the central axis C.

Figure 4A:
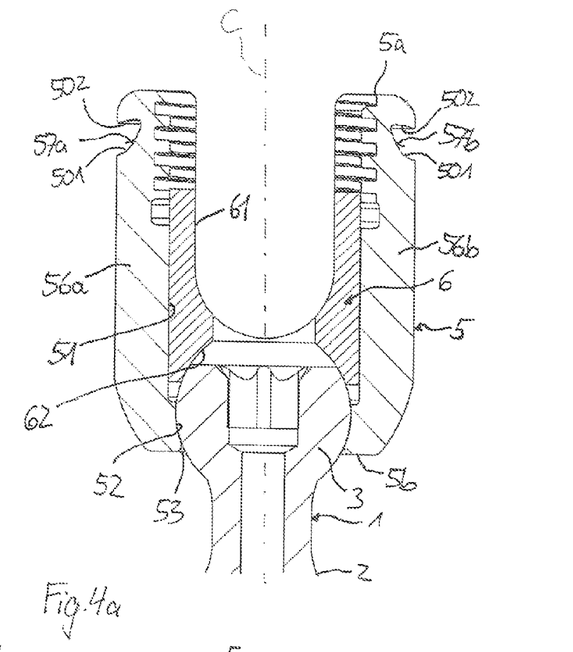
FIG. 4a shows a cross-sectional view of the bone anchoring device of FIGS. 1 to 3, where the cross-section is taken along line A-A in FIG. 3.
Figure 4B:
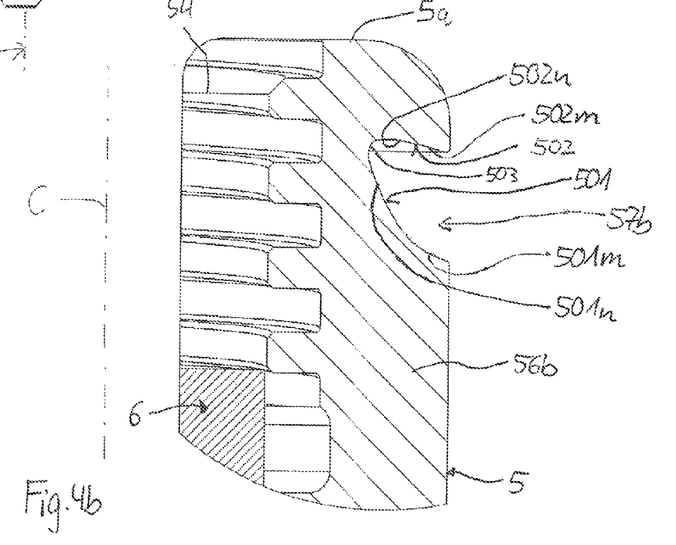

Referring to FIGS. 4a and 4b, the shape of the grooves 57a, 57b is further described in more detail. The surface forming the grooves 57a, 57b is entirely curved, for example, by curved portions without any flat portions between the curved portions. In a cross-sectional view, a contour of the surface forming each groove 57a, 57b forms an arcuate line with a first arcuate portion 501 and a second arcuate portion 502 opposing the first arcuate portion 501. The arcuate line is substantially free from straight portions, and in particular, between the first arcuate portion 501 and the second arcuate portion 502. The first arcuate portion 501 is at a greater distance from the first end 5a than a distance between the second arcuate portion 502 and the first end 5a. In the cross-sectional views of FIGS. 4a and 4b, the first arcuate portion 501 is concave and the second arcuate portion 502 is concave. Moreover, the first arcuate portion 501 rises constantly from the exterior surface of each respective leg 56a, 56b towards the first end 5a of the receiving part 5. The second arcuate portion 502 also rises constantly from the exterior surface of each respective leg 56a, 56b towards the first end 5a of the receiving part. Preferably, the rise of the first arcuate portion 501 is steeper than the rise of the second arcuate portion 502. Hence, in the cross-sectional views of FIGS. 4a and 4b, the contour of the arcuate line may resemble a saw-tooth where all straight or angled portions are rounded.

Moreover, the first arcuate portion 501 may include sub-portions 501m, 501n having different radii of curvature. For example, the first sub-portion 501m, which is closer to the exterior surface of the receiving part 5, may have a smaller radius of curvature than the second sub-portion 501n, which is farther away from the exterior surface. This may be similar for the second arcuate portion 502. The sub-portions constantly adjoin each other.

The first arcuate portion 501 and the second arcuate portion 502 are in communication with each other through a third arcuate portion 503 that is farthest away in a radial direction from the exterior surface of each leg 56a, 56b and that has a smaller radius of curvature than the first arcuate portion 501 and the second arcuate portion 502.

As can be seen in FIGS. 1 to 3, the cross-section of each groove 57a, 57b is the same along the entire length of the grooves 57a, 57b. Also, the grooves 57a, 57b on each leg 56a, 56b have a mirror symmetrical shape.

Turning again to FIGS. 1 and 4a, the pressure element 6 is a substantially cylindrical part that has an outer diameter that is only slightly smaller than an inner diameter of the coaxial bore 51 of the receiving part 5. A U-shaped recess 61 for receiving the spinal fixation element is provided that is, in the assembled state, aligned with the U-shaped recess 55 of the receiving part 5. At a side of the pressure element 6 facing the head 3, a substantially spherical recess 62 is provided for contacting the head 3 (FIG. 4a). In addition, a coaxial bore 63 may be provided for allowing access to the head 3 with a driver.

Figures 5, 6A, 6B:
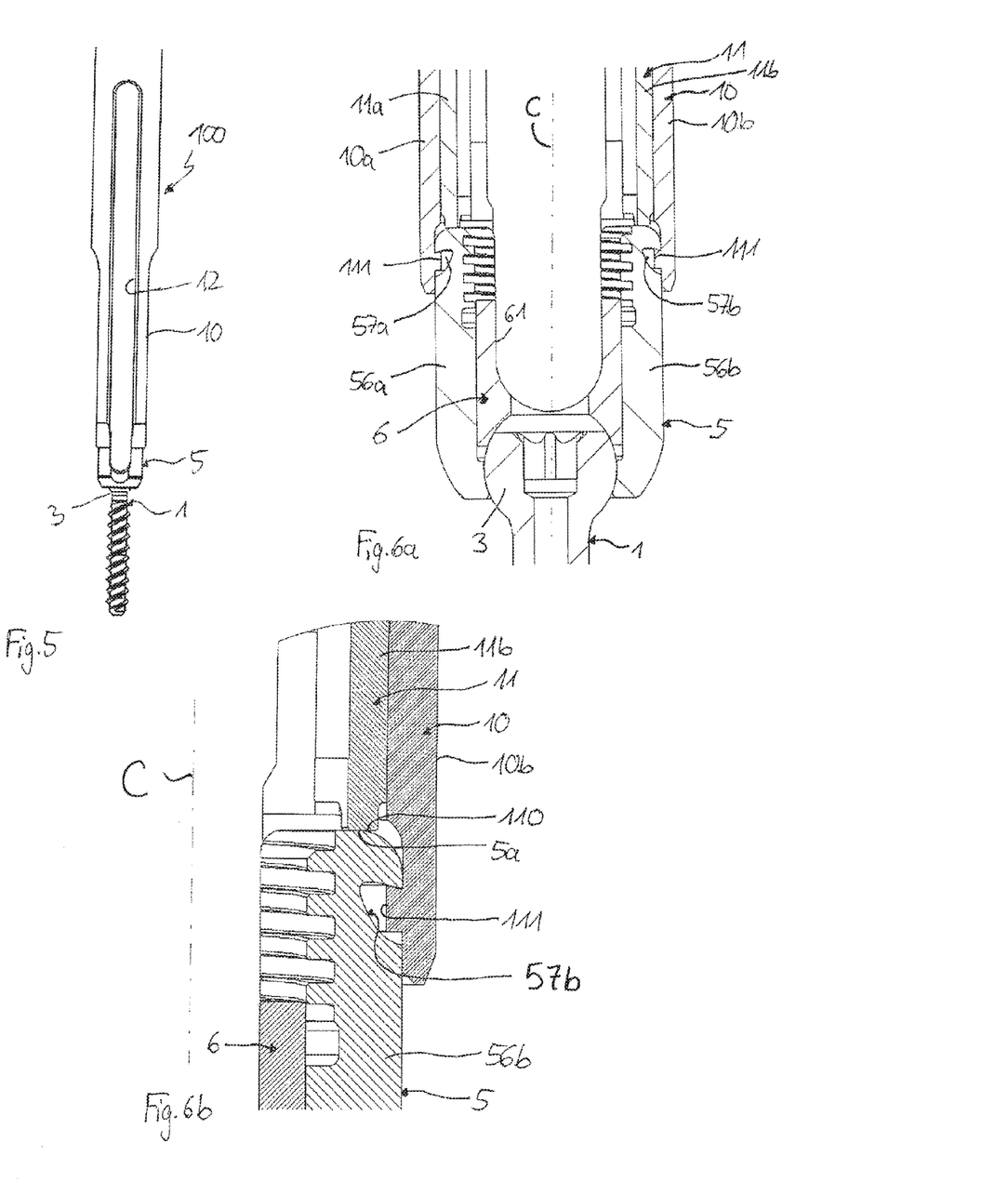
Figures 7, 8:
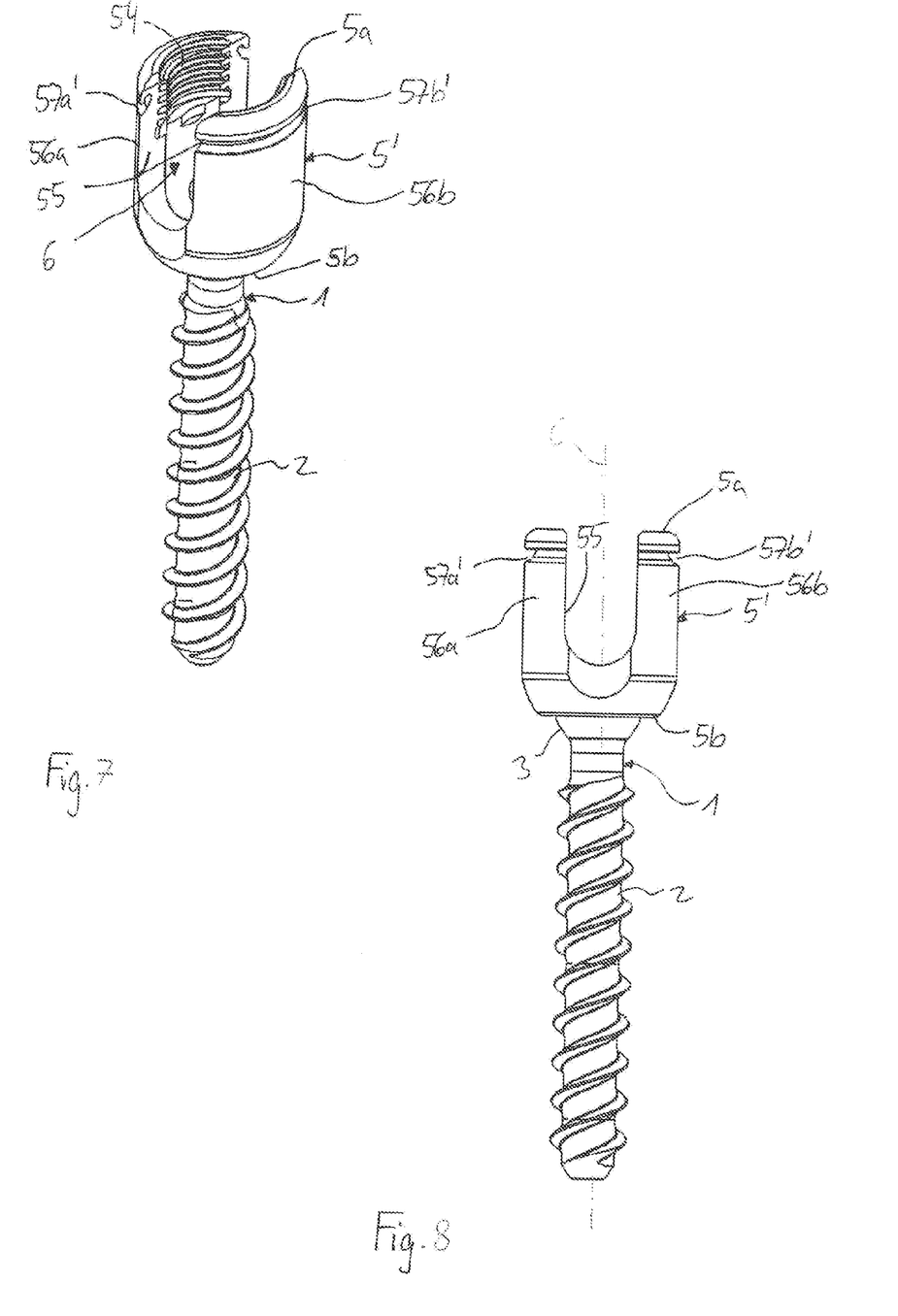
FIG. 7 shows a perspective view of a second embodiment of a bone anchoring device with a receiving part in an assembled state.
FIG. 8 shows a front view of the bone anchoring device of FIG. 7.

Referring to FIGS. 5 to 6b, an instrument 100, such as an extension device, is provided for use with the bone anchoring device, in particular, for use in minimally invasive surgery. The instrument 100 includes a first sleeve 10 that forms an outer sleeve, a second sleeve 11 that forms an inner sleeve and that is positionable within the first sleeve 10, and a mechanism (not shown) for displacing the second sleeve 11 relative to the first sleeve 10 in an axial direction. When the first sleeve 10 and the second sleeve 11 are assembled, the extension device can be used to place the parts of a spinal stabilization system in a patient's body using a minimally invasive procedure. Each of the first sleeve 10 and the second sleeve 11 has elongate substantially U-shaped slits 12 that have a reverse U-shape compared to the recess 55 in the receiving part 5, such that the first sleeve 10 and the second sleeve 11 are each separated into two arms 10a, 10b, 11a, 11b, respectively, that are configured to engage the corresponding legs 56a, 56b of the receiving part 5. The slits 12 have a width in a circumferential direction that is greater than a diameter of the spinal fixation element, such that the slits 12 permit the spinal fixation element to be passed through the slits 12. Due to the slits 12, the arms of the first sleeve 10 are slightly flexible in a direction perpendicular to the sleeve axis, such that the first sleeve 10 can be snapped onto the legs 56a, 56b of the receiving part 5. A free end surface 110 of the second sleeve 11 is configured to contact the first end 5a of the receiving part 5. At a distance from a free end of the first sleeve 10, a circumferential inner projection 111 is provided that is configured to engage the grooves 57a, 57b. The shape of the circumferential projection 111 may be any shape that is suitable to engage the grooves 57a, 57b. However, the shape of the circumferential projection 111 does not need to have the same shape as the shape of the grooves 57a, 57b (see FIG. 6b). This allows using other instruments with different shapes in combination with the bone anchoring device.

The parts of the bone anchoring device can be made of a bio-compatible material, such as a bio-compatible metal, a bio-compatible metal alloy, for example, stainless steel, titanium, nickel-titanium (NiTi) alloys, such as Nitinol, magnesium or magnesium alloys, or from a bio-compatible plastic material, such as, for example, polyether ether ketone (PEEK) or poly-l-lactide acid (PLLA). The parts can be made of the same material or of different materials.

In clinical use, the extension device is attached to the receiving part 5 of the bone anchoring device. The bone anchoring device may be implanted through a minimally invasive procedure, for example, into a pedicle of a vertebra. The instrument may be connected to the bone anchoring device either before or after implantation of the bone anchoring device into a patient's body. The attachment of the instrument to the receiving part is achieved by first moving the first sleeve 10 towards the receiving part 5. When the arms 10a, 10b of the first sleeve 10 contact and are pushed against the first end 5a of the receiving part 5, the arms 10a, 10b are spread to a certain extent and the projections 111 snap into the grooves 57a, 57b by a further downward movement. The engagement of the grooves 57a, 57b by the instrument is facilitated by the curved surface of the grooves 57a, 57b. Because of the curved surface of the grooves 57a, 57b, notching effects and jamming are prevented and the engagement projection 111 of the instrument slides smoothly into the grooves 57a, 57b. At the same time, due to the structure of the grooves 57a, 57b, inadvertent disengagement of the instrument from the receiving part 5 can be prevented.

Then, the second sleeve 11 is moved relative to the first sleeve 10 towards the receiving part 5 until the free end surface 110 of the second sleeve 11 presses onto the first end 5a of the receiving part 5. Thereby, the receiving part 5 is firmly held by the arms 10a, 10b, 11a, 11b of the first sleeve 10 and the second sleeve 11, respectively, of the instrument.

A plurality of bone anchoring devices may be implanted in a surgical procedure, and each receiving part of the plurality of bone anchoring devices may be connected to a separate extension device. By rotating the extension devices, the U-shaped recesses 55 of the receiving parts 5 of the plurality of bone anchors can be aligned to permit insertion of a rod therein. The rod can be inserted through the slits 12 of the extension devices and placed into the U-shaped recesses 55 of the receiving parts 5. The rod can be fixed with a locking element that is guided through the extension device until the locking element can be screwed between the legs 56a, 56b of the receiving part 5. With the extension devices, compression or distraction procedures can be performed using minimally invasive techniques.

Figures 9A, 9B:
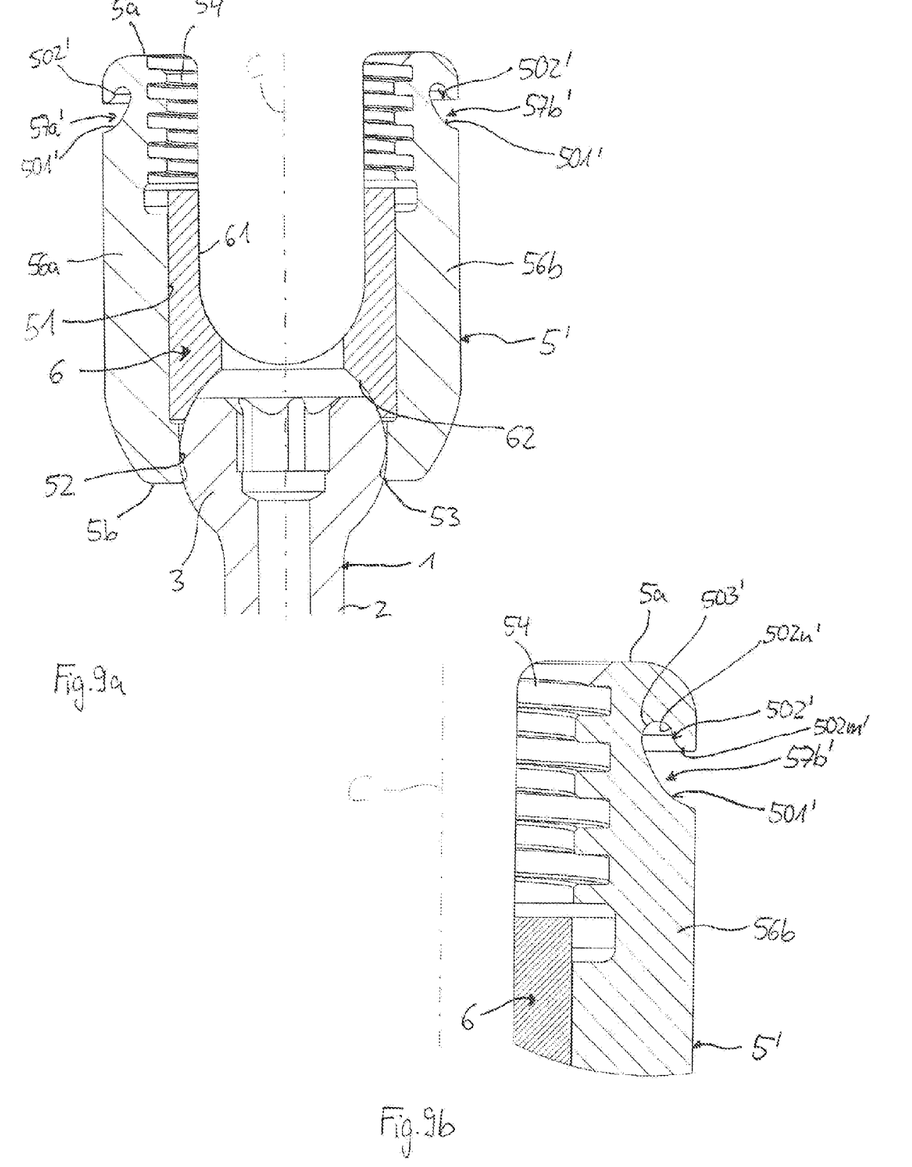
Figures 10, 11:
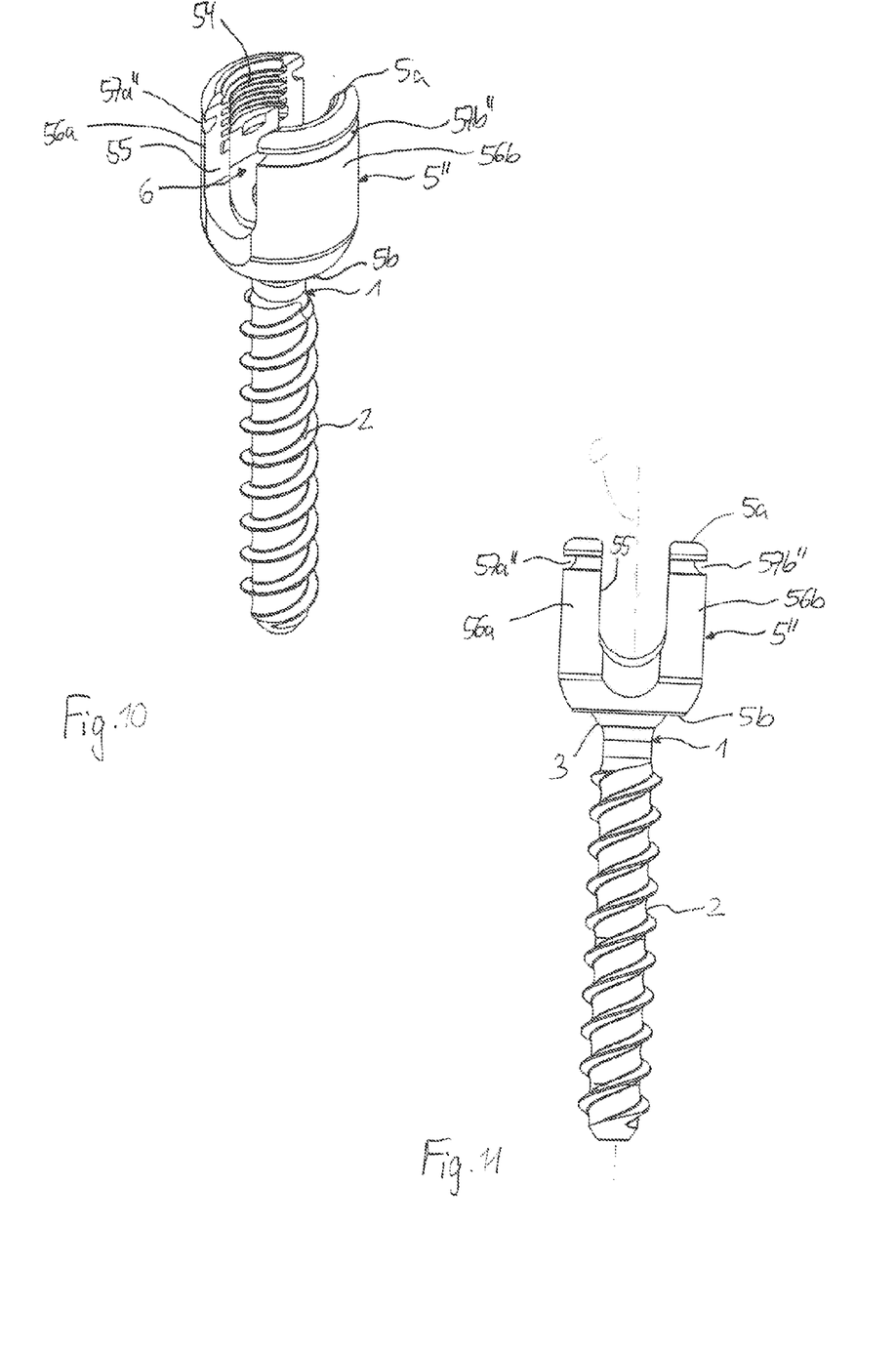
FIG. 10 shows a perspective view of a third embodiment of a bone anchoring device with a receiving part in an assembled state.
FIG. 11 shows a front view of the bone anchoring device of FIG. 10.
Figures 12A, 12B:
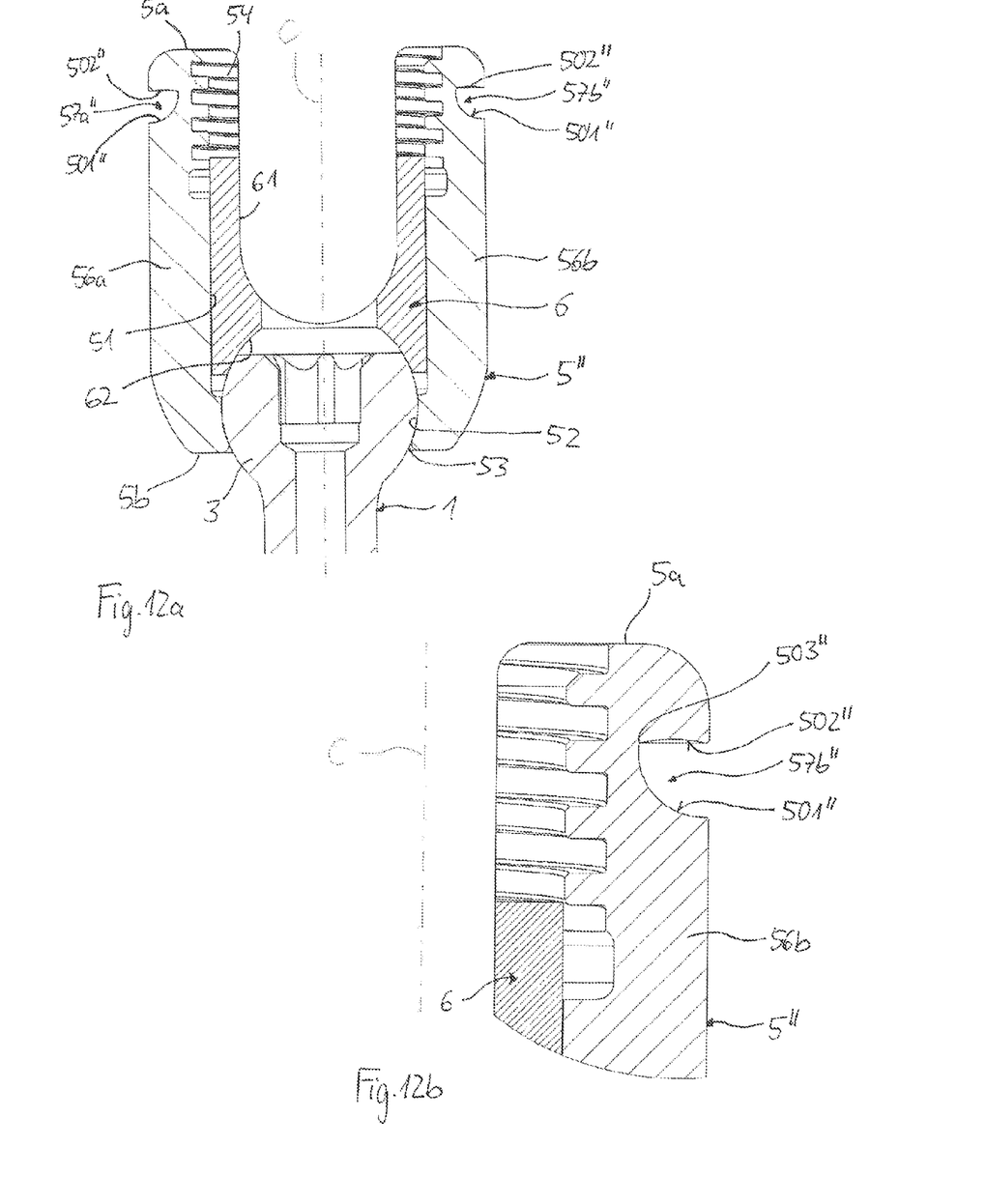

Referring to FIGS. 7 to 9b, a second embodiment of a bone anchoring device having a receiving part 5' will be described. Parts and portions that are identical or similar to the first embodiment are marked with the same reference numerals, and the description thereof is not repeated. The receiving part 5' includes grooves 57a', 57b' with an undercut seen from the exterior surface of the legs 56a, 56b. The first arcuate portion 501' of each of the grooves 57a', 57b' may be similar to that of the first embodiment. In a cross-sectional view as depicted in FIGS. 9a and 9b, the second arcuate portion 502' includes a first sub-portion 502m', which is convex, and a second sub-portion 502n', which is concave. As a result, the second arcuate portion 502' has a similar steepness as compared to the first arcuate portion 501' and an undercut is provided by the change of the radii of curvature of the sub-portions 502m', 502n'. A third arcuate portion 503' may have a same radius of curvature as the second sub-portion 502n' and may continue directly into the first arcuate portion 501'. This shape of the grooves 57a', 57b' can further reduce the risk of inadvertent disengagement of the instrument from the receiving part 5'.

Referring to FIGS. 10 to 12b, a third embodiment of a bone anchoring device having a receiving part 5" will be described. Parts and portions that are similar or identical to the previous embodiments are marked with the same reference numerals and the description thereof is not repeated. The receiving part 5" of the third embodiment differs from the receiving part of the previous embodiments by the shape of the grooves 57a", 57b". More in detail, the first arcuate portion 501" has a single radius of curvature such that the entire first arcuate portion 501" forms a segment of a circle. Compared to the previous embodiments, the radius of curvature of the first arcuate portion 501" is smaller than that of the first arcuate portions of the previous embodiments. The second arcuate portion 502" has a considerably greater radius of curvature than the radius of curvature of the first arcuate portion 501". Also, a length of the second arcuate portion 502" is considerably shorter than a length of the first arcuate portion 501". The third arcuate portion 503", which forms a transition between the first arcuate portion 501" and the second arcuate portion 502", has a considerably smaller radius of curvature than the first and second arcuate portions such that the transition has the shape of a rounded corner, for example, a rounded, nearly 90° corner. This design provides guidance for the instrument via the first arcuate portion 501" and facilitates disengagement of the instrument from the receiving part 5" by the slightly arcuate second arcuate portion 502".

Figure 13:
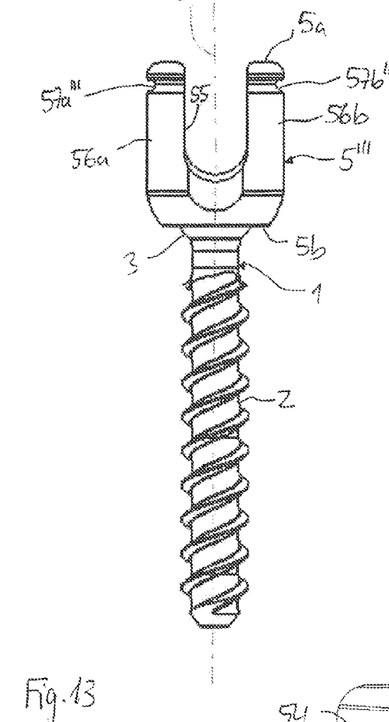
FIG. 13 shows a front view of a bone anchoring device with a receiving part according to a fourth embodiment.
Figure 14A:
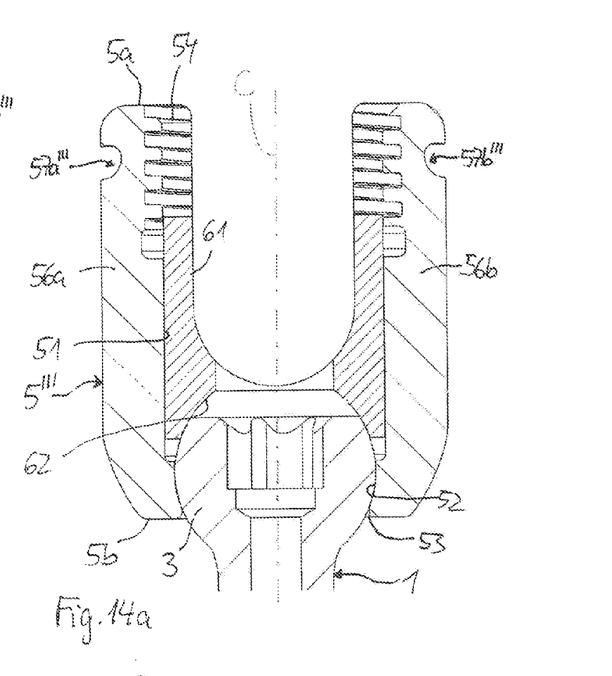
FIG. 14a shows a cross-sectional view of the bone anchoring device of FIG. 13, where the cross-section is taken in a plane including a central axis of the receiving part and extending through centers of the legs of the receiving part.
Figure 14B:
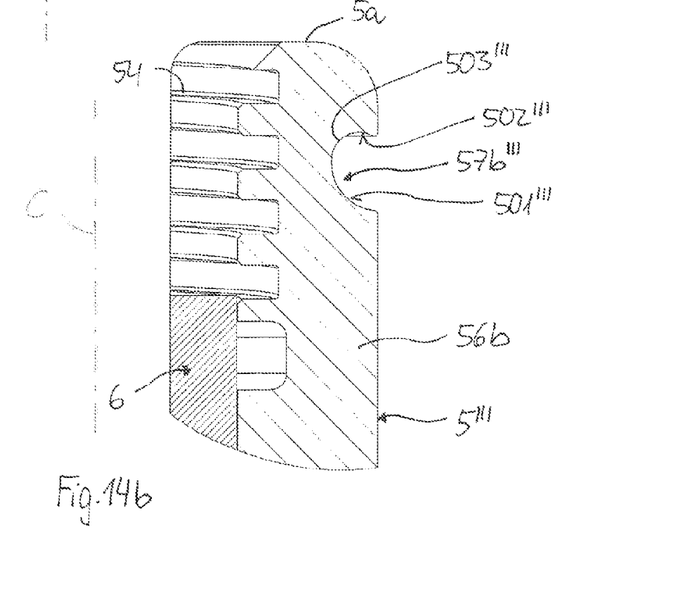

Referring to FIGS. 13 to 14b, a fourth embodiment of a bone anchoring device having a receiving part is described. Parts and portions that are identical or highly similar to that of the previous embodiments are marked with the same reference numerals and the description thereof is not repeated. The receiving part 5"" of the fourth embodiment differs from the receiving parts of the previous embodiments in the shape of the grooves 57a'", 57b'". The grooves 57a'", 57b'" each include a first arcuate portion 501'" with a single radius of curvature, and opposite thereto a second arcuate portion 502'" with a single radius of curvature that is considerably smaller than the radius of curvature of the first arcuate portion 501'". Each of the grooves 57a'", 57b" further includes a transition portion 503'" with a radius of curvature that is between the radius of curvature of the first arcuate portion 501'" and the radius of curvature of the second arcuate portion 502'". A contour of the arcuate line formed by the grooves 57a'", 57b" resembles a deformed circle segment wherein the first arcuate portion 501'" is slightly bent outward. This design allows an easy snap-in of the instrument into the grooves 57a'", 57b" and also prevents notching effects.

Figure 15:
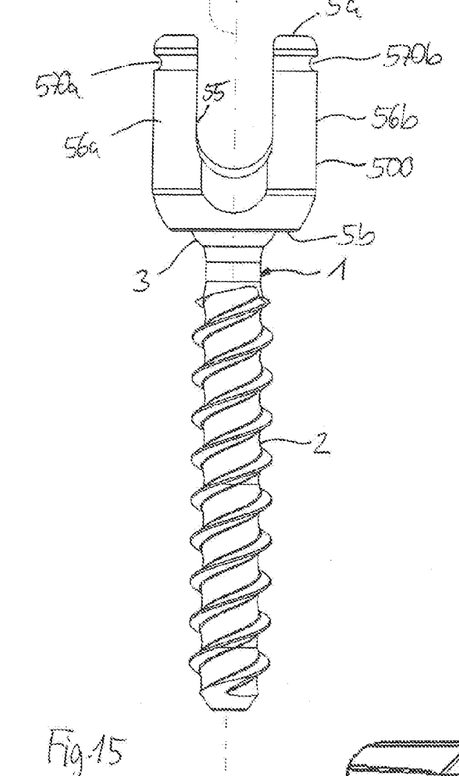
FIG. 15 shows a front view of a fifth embodiment of a bone anchoring device with a receiving part.
Figure 16A:
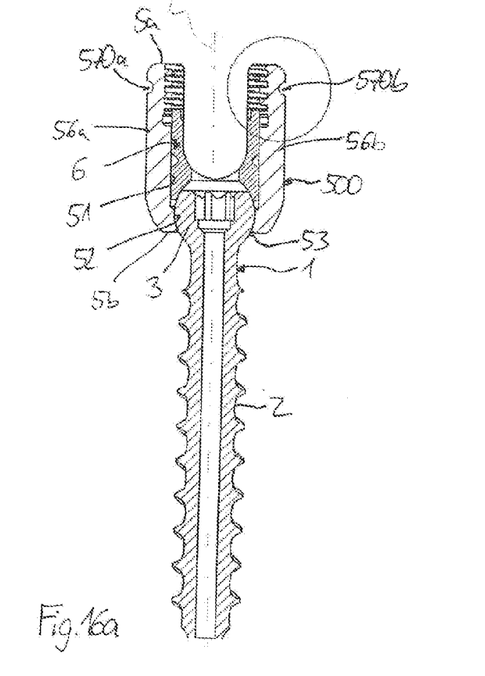
FIG. 16a shows a cross-sectional view of the bone anchoring device of FIG. 15, where the cross-section is taken in a plane including a central axis of the receiving part and extending through centers of the legs of the receiving part.
Figure 16B:
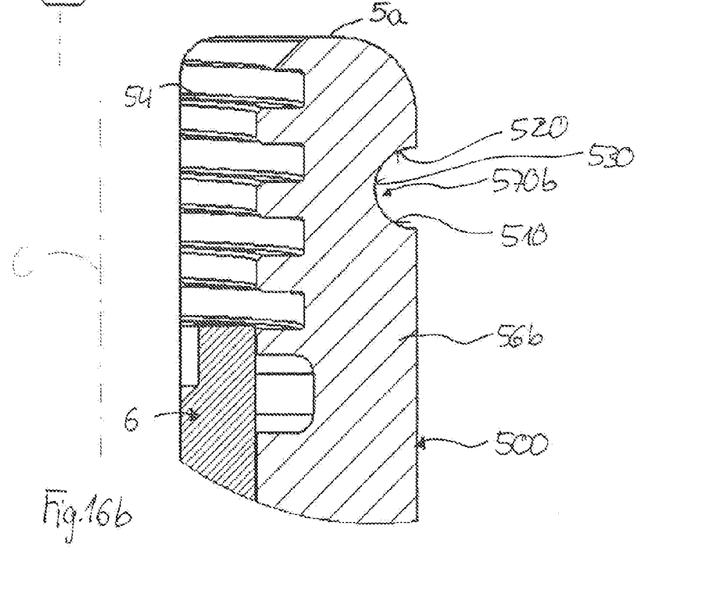

A fifth embodiment of the bone anchoring device will be described with reference to FIGS. 15 to 16b. The receiving part 500 of the fifth embodiment differs from the receiving parts of the previous embodiments by the shape of the grooves 570a, 570b. The grooves 570a, 570b have, in a cross-sectional view, a contour of a segment of a circle. Hence, the first arcuate surface portion 510, the second arcuate surface portion 520, and the third arcuate surface portion 530 all have identical radii of curvature and the same center of curvature. This design is particularly easy to manufacture and also prevents notching effects.

Modifications of the above-described embodiments are conceivable. While the embodiments show a particular type of receiving part which permits the bone anchoring element to be inserted therein from the first end of the receiving part, a so-called top-loading polyaxial bone anchoring device, any other type of receiving part may be provided having grooves according to the embodiments described. Such other embodiments of receiving parts may be bottom-loading receiving parts, where the lower opening of the receiving part is large enough to insert the bone anchoring element therein from the bottom end of the receiving part. This may be particularly useful for polyaxial bone anchoring devices where the bone anchoring element is first implanted into a bone and the receiving part is mounted to the bone anchoring element thereafter. Other types of receiving parts may include a receiving part with an inner compression member or a receiving part using an outer ring to compress the head of the bone anchoring element to lock an angular position of the bone anchoring element relative to the receiving part. While the embodiments show a polyaxial bone anchoring device, the receiving part may also be a receiving part of a monoaxial bone anchoring device, having a shank that is fixedly connected to the receiving part. Also, monoplanar bone anchoring devices that permit the anchoring element to pivot only in a single plane may be provided with the grooves. In addition, receiving parts that allow a greater pivot angle of the bone anchoring element to one side or an adjustable greater pivot angle may be provided with the grooves according to the embodiments.

The shank of the bone anchoring element can have any suitable shape and structure for anchoring in the bone, such as a threaded shank, a shank with barbs, a nail, a cannulated shank with or without openings in the wall, a non-cannulated shank, and the like. For polyaxial bone anchoring devices, the head of the bone anchoring element can have any shape that allows pivoting in the receiving part.

In a further modification, the grooves may end at a distance from the U-shaped recess in the circumferential direction. For particular applications, the grooves may have a different shape on one leg as compared to the other leg. In particular, any shape of the grooves described above may be provided on one leg and another shape of the grooves described above may be provided on the other leg.

The bone anchoring device with the receiving part and the system of an instrument with the bone anchoring device are not limited to use in minimally invasive surgery, but can also be used in conjunction with all other surgical procedures and/or minimally open surgical procedures.

It shall be noted that features of the embodiments described above can be combined with features of other embodiments, mixed and matched to produce a variety of further embodiments.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

The invention claimed is:

1. A receiving part of a bone anchoring device comprising:
   a first end;
   a second end opposite to the first end;
   a central axis extending through the first end and the second end;
   a substantially U-shaped-recess adjacent to the first end for receiving a spinal fixation element, wherein the substantially U-shaped recess forms two free legs;
   a bore extending from the first end towards the second end and in communication with the substantially U-shaped recess; and
   a groove in an outer surface of each of the legs, wherein each of the grooves has a first end and a second end and extends in a circumferential direction in an arcuate shape around the central axis between the first end of the groove and the second end of the groove;
   wherein in a plane that includes the central axis and that extends through a center of each leg, a contour of a resulting cross-section of each of the grooves viewed in the plane is defined by an entirely curved first arcuate portion, an entirely curved second arcuate portion opposing the first arcuate portion, and an entirely curved profile having one end directly connected to the first arcuate portion and an opposite end directly connected to the second arcuate portion; and
   wherein the contour of the resulting cross-section of each of the grooves viewed in the plane comprises more than one radius of curvature.

2. The receiving part of claim 1, wherein for each of the grooves, the second arcuate portion is between the first end of the receiving part and the first arcuate portion, and wherein the second arcuate portion rises constantly from the outer surface of the corresponding leg towards the first end of the receiving part.

3. The receiving part of claim 2, wherein the second arcuate portion rises less steeply than the first arcuate portion.

4. The receiving part of claim 1, wherein for each of the grooves, the first arcuate portion has a first radius of curvature and the second arcuate portion has a second radius of curvature, and wherein the entirely curved profile comprises a third arcuate portion that is located farthest from the outer surface of the corresponding leg relative to the first and second arcuate portions in a direction perpendicular to the central axis and that has a third radius of curvature of which is smaller than the first radius of curvature.

5. The receiving part of claim 4, wherein the third radius of curvature is smaller than the second radius of curvature.

6. The receiving part of claim 1, wherein for each of the grooves, the first arcuate portion rises constantly from the outer surface of the corresponding leg towards the first end of the receiving part.

7. The receiving part of claim 1, wherein the grooves extend in a circumferential direction along an entire width of the legs and are open towards the substantially U-shaped recess.

8. The receiving part of claim 1, wherein the second arcuate portion is convex.

9. The receiving part of claim 1, wherein the second arcuate portion is concave.

10. The receiving part of claim 1, wherein the second arcuate portion is convex and is followed by a concave arcuate portion, forming an undercut.

11. The receiving part of claim 1, wherein the first arcuate portion has more than one radius of curvature.

12. The receiving part of claim 1, wherein the second arcuate portion comprises more than one radius of curvature.

13. The receiving part of claim 1, wherein a contour of each of the grooves is the same over an entire length of the groove in the circumferential direction.

14. The receiving part of claim 1, wherein the contour of the resulting cross-section of each of the grooves comprises an upper end adjacent the outer surface of the leg and a lower end adjacent the outer surface of the leg, and wherein the first arcuate portion comprises the lower end and the second arcuate portion comprises the upper end.

15. The receiving part of claim 1, wherein the contour of the resulting cross-section of each of the grooves viewed in the plane comprises a convex portion and a concave portion.

16. A bone anchoring device comprising:
a bone anchoring element having a shank for anchoring to a bone; and
a receiving part comprising:
a first end;
a second end opposite to the first end;
a central axis extending through the first end and the second end;
a substantially U-shaped-recess adjacent to the first end for receiving a spinal fixation element, wherein the substantially U-shaped recess forms two free legs;
a bore extending from the first end towards the second end and in communication with the substantially U-shaped recess; and
a groove in an outer surface of each of the legs, wherein each of the grooves has a first end and a second end and extends in a circumferential direction in an arcuate shape around the central axis between the first end of the groove and the second end of the groove;
wherein in a plane that includes the central axis and that extends through a center of each leg, a contour of a resulting cross-section of each of the grooves viewed in the plane is defined by an entirely curved first arcuate portion, an entirely curved second arcuate portion opposing the first arcuate portion, and an entirely curved profile having one end directly connected to the first arcuate portion and an opposite end directly connected to the second arcuate portion; and
wherein the contour of the resulting cross-section of each of the grooves viewed in the plane comprises more than one radius of curvature.

17. The bone anchoring device of claim 16, wherein for each of the grooves, the first and second arcuate portions each extends to the outer surface of the corresponding leg.

18. The bone anchoring device of claim 17, wherein the entirely curved profile comprises a third arcuate portion joining the first arcuate portion to the second arcuate portion.

19. A bone anchoring device system comprising:
a receiving part of a bone anchoring device comprising:
a first end;
a second end opposite to the first end;
a central axis extending through the first end and the second end;
a substantially U-shaped-recess adjacent to the first end for receiving a spinal fixation element, wherein the substantially U-shaped recess forms two free legs;
a bore extending from the first end towards the second end and in communication with the substantially U-shaped recess; and
a groove in an outer surface of each of the legs, wherein each of the grooves has a first end and a second end and extends in a circumferential direction in an arcuate shape around the central axis between the first end of the groove and the second end of the groove;
wherein in a plane that includes the central axis and that extends through a center of each leg, a contour of a resulting cross-section of each of the grooves viewed in the plane is defined by an entirely curved first arcuate portion, an entirely curved second arcuate portion opposing the first arcuate portion, and an entirely curved profile having one end directly connected to the first arcuate portion and an opposite end directly connected to the second arcuate portion; and
wherein the contour of the resulting cross-section of each of the grooves viewed in the plane comprises more than one radius of curvature; and
an instrument, wherein the instrument comprises a first sleeve having two arms, wherein each arm comprises a protrusion configured to engage the grooves.

20. The bone anchoring device system of claim 19, wherein the protrusions have a contour that is different from a contour of the grooves.

21. A method of connecting an instrument to a bone anchoring device, wherein the bone anchoring device comprises a receiving part comprising a first end, a second end opposite to the first end, a central axis extending through the first end and the second end, a substantially U-shaped-recess adjacent to the first end for receiving a spinal fixation element, wherein the substantially U-shaped recess forms two free legs, a bore extending from the first end towards the second end and in communication with the substantially U-shaped recess, and a groove in an outer surface of each of the legs, wherein each of the grooves has a first end and a second end and extends in a circumferential direction in an arcuate shape around the central axis between the first end of the groove and the second end of the groove, wherein in a plane that includes the central axis and that extends through a center of each leg, a contour of a resulting cross-section of each of the grooves viewed in the plane is defined by an entirely curved first arcuate portion, an entirely curved second arcuate portion opposing the first arcuate portion, and an entirely curved profile having one end directly connected to the first arcuate portion and an opposite end directly connected to the second arcuate portion, and wherein the contour of the resulting cross-section of each of the grooves viewed in the plane comprises more than one radius of curvature, the instrument comprising a first sleeve having two arms and a second sleeve positionable within the first sleeve, wherein each arm of the first sleeve comprises a protrusion configured to engage the grooves, the method comprising:
  engaging the grooves of the receiving part with the protrusions of the first sleeve of the instrument; and
  contacting the receiving part with the second sleeve of the instrument.

* * * * *